(12) United States Patent
Bektesevic et al.

(10) Patent No.: US 9,309,175 B2
(45) Date of Patent: Apr. 12, 2016

(54) REACTION SYSTEM AND PROCESS TO PRODUCE FLUORINATED ORGANICS

(71) Applicant: HONEYWELL INTERNATIONAL INC., Morristown, NJ (US)

(72) Inventors: Selma Bektesevic, Williamsville, NY (US); Haluk Kopkalli, Staten Island, NY (US); Haiyou Wang, Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 14/353,182

(22) PCT Filed: Apr. 18, 2014

(86) PCT No.: PCT/US2014/034580
§ 371 (c)(1),
(2) Date: Apr. 21, 2014

(87) PCT Pub. No.: WO2014/172592
PCT Pub. Date: Oct. 23, 2014

(65) Prior Publication Data
US 2015/0057472 A1     Feb. 26, 2015

Related U.S. Application Data

(60) Provisional application No. 61/813,393, filed on Apr. 18, 2013.

(51) Int. Cl.
| | |
|---|---|
| *C07C 17/25* | (2006.01) |
| *C07C 17/20* | (2006.01) |
| *C07C 17/38* | (2006.01) |
| *B01J 23/26* | (2006.01) |
| *C07C 17/087* | (2006.01) |
| *B01D 45/02* | (2006.01) |
| *B01J 12/00* | (2006.01) |
| *B01J 37/26* | (2006.01) |

(52) U.S. Cl.
CPC .............. *C07C 17/202* (2013.01); *B01D 45/02* (2013.01); *B01J 12/007* (2013.01); *B01J 23/26* (2013.01); *B01J 37/26* (2013.01); *C07C 17/087* (2013.01); *C07C 17/206* (2013.01); *C07C 17/25* (2013.01); *C07C 17/38* (2013.01)

(58) Field of Classification Search
CPC ...... C07C 17/25; C07C 17/093; C07C 17/20; C07C 17/206
See application file for complete search history.

(56) References Cited

U.S. PATENT DOCUMENTS

| | | | | |
|---|---|---|---|---|
| 3,410,057 A | * | 11/1968 | Lerner | ............................. 95/274 |
| 4,752,307 A | * | 6/1988 | Asmus et al. | ................... 95/213 |
| 5,695,548 A | * | 12/1997 | Trutna | ............................. 95/216 |
| 5,710,352 A | | 1/1998 | Tung | |
| 6,388,155 B1 | | 5/2002 | Sy et al. | |
| 7,137,622 B2 | * | 11/2006 | Buchanan | ................... 261/114.1 |
| 7,795,480 B2 | * | 9/2010 | Merkel et al. | ................. 570/155 |
| 2001/0034465 A1 | | 10/2001 | Swain et al. | |
| 2010/0036179 A1 | * | 2/2010 | Merkel et al. | ................. 570/156 |
| 2011/0105807 A1 | | 5/2011 | Kopkalli et al. | |
| 2011/0245548 A1 | | 10/2011 | Merkel et al. | |

OTHER PUBLICATIONS

International Search Report and Written Opinion dated Aug. 12, 2014, issued in International Application No. PT/US2014/034580.

* cited by examiner

*Primary Examiner* — Jafar Parsa
*Assistant Examiner* — Medhanit Bahta
(74) *Attorney, Agent, or Firm* — Scully Scott Murphy and Presser

(57) ABSTRACT

The invention relates to the use of a liquid-vapor separator such as a de-entrainer to remove an unvaporized portion of a feed, e.g. 1,1,2,3-tetrachloropropene (1230xa), to a catalytic vapor phase fluorination reaction where e.g. 2-chloro-3,3,3,-trifluoropropene (1233xf) is produced. The invention extends the life of the catalyst.

16 Claims, No Drawings

REACTION SYSTEM AND PROCESS TO PRODUCE FLUORINATED ORGANICS

CROSS-REFERENCE TO RELATED APPLICATIONS

This application claims the benefit of U.S. Provisional Application No. 61/813,393 filed on Apr. 18, 2013, the entire contents of which are incorporated herein by reference.

FIELD OF THE INVENTION

The invention relates to a reaction system and process for preparing fluorinated organic compounds; more particularly, a reaction system comprising a de-entrainer useful, e.g. in a process to produce compounds such as 2-chloro-3,3,3,-trifluoropropene (1233xf) which can be used in the manufacture of 2,3,3,3-tetrafluoropropene (HFO-1234yf).

BACKGROUND OF THE INVENTION

Hydrofluoroolefins (HFOs), such as tetrafluoropropenes (including 2,3,3,3-tetrafluoropropene (HFO-1234yf)), are known to be effective refrigerants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFOs do not contain chlorine and, thus, pose no threat to the ozone layer. HFO-1234yf has also been shown to be a low global warming compound with low toxicity and, hence, can meet increasingly stringent requirements for refrigerants in mobile air conditioning. Accordingly, compositions containing HFO-1234yf are among the materials being developed for use in many of the aforementioned applications.

One manufacturing process for HFO-1234yf, as disclosed in U.S. Pat. No. 8,058,486, the contents of which are incorporated herein by reference, uses 1,1,2,3-tetrachloropropene (1230xa) as starting raw material. The process consists of the following three steps:

1) 1230xa+3HF→2-chloro-3,3,3,-tritluoropropene (HCFO-1233xf)+3HCl in a vapor phase reactor charged with a solid catalyst,
2) 1233xf+HF→2-chloro-1,1,1,2-tetrafluoropropane (HCFC-244bb) in a liquid phase reactor charged with a liquid catalyst; and
3) 244bb→2,3,3,3-tetrafluoropropene (HFO-1234yf)+HCl in a vapor phase reactor.

In one process, Step (1) occurs in the presence of fluorination catalyst, such as chromium oxide and the like, as known in the art. While this catalyst is generally quite active and selective, it tends to deactivate (lose activity) slowly over time during the course of the reaction. Deactivation, in turn, leads to yield loss and a process that is economically disadvantageous.

Thus, there is a continuing need for a reactor systems and processes that extend catalyst life and stability in, among other things, the conversion of 1230xa to 1233xf.

SUMMARY OF THE INVENTION

The invention relates in one embodiment to a reactor system comprising: a vaporizer; a de-entrainer in fluid communication with said vaporizer, the de-entrainer having a vapor outlet; and a vapor phase reactor in fluid communication with the vapor outlet of the de-entrainer. De-entrainers contemplated by the invention include, e.g. liquid-vapor separators, including without limitation, towers such as packed towers and trayed towers, knock out pots, filters, and the like, or combinations thereof.

The invention also relates to a process to prepare fluorinated organics such as 2-chloro-3,3,3,-trifluoropropene (1233xf) comprising: (a) providing a starting material comprising liquid 1,1,2,3-tetrachloropropene (1230xa) and vaporous 1230xa; (b) separating the vaporous 1230xa from the liquid 1230xa, in e.g. a de-entrainer; and (c) contacting the vaporous 1230xa with hydrogen fluoride HF under conditions effective to form 1233xf. The 1233xf thus produced may be used as the feed material to form other fluorinated organics, such as 244bb, which in turn can be used to form 1234yf.

Inasmuch as it has been found that unvaporized (liquid) feed, such as 1230xa, could entrain with vaporized liquid, such as 1230xa, and thereafter play a role in catalyst deactivation, the present invention beneficially extends catalyst life by removing substantially all of the unvaporized (liquid) feed, such as 1230xa, prior to catalyst contact. In a preferred practice, the feed is 1230xa and contacts the catalyst in the vaporous state. Thus, without limitation, the invention improves catalyst stability by using a feed, such as 1230xa, that is in substantially or pure vapor form.

DETAILED DESCRIPTION OF THE INVENTION

The foregoing summary and general description of the invention and the ensuing detailed description are exemplary and explanatory and are not restrictive of the invention, as defined in the appended claims. Other features and embodiments and modifications will be apparent from the present description and are within the scope of the invention. The entire contents of U.S. Pat. Nos. 8,258,355 and 8,084,653, are incorporated herein by reference.

In one embodiment, the invention relates to a reactor system comprising a vaporizer; a de-entrainer (which term includes one or more de-entrainers which can be the same or different) in fluid communication with said vaporizer, wherein the de-entrainer that has a vapor outlet and preferably a liquid outlet; and a vapor phase reactor, such as a fluorination reactor, in fluid communication with the vapor outlets of the de-entrainer. Preferably, the de-entrainer comprises a liquid-vapor separator as known in the art, including without limitation, towers such as a packed tower, a trayed tower, a knock out pot, a filter device, or combinations thereof.

In one practice, the de-entrainer comprises a knock-out pot (which term includes one or more knock-pots which can be the same or different) which may be used alone or in combination with another de-entrainer; the knock-out pot can be one with or without internals such as, e.g., a colaescer for scrubbing out liquid particles from the fluid feed, such as 1203xa which is substantially vapor but contains some 1230xa in the unvaporized state; in a preferred practice, the de-entrainer is a knock-out pot comprising an internal coalescer, such as packing (e.g. Pall rings), mesh, and the like, and combinations thereof. Without limitation, the knock-out pot is preferably of cylindrical shape with an inlet, e.g. in fluid communication with the vaporizer, and two outlets: one a vapor outlet in fluid communication, e.g. with the reactor, and the other a liquid outlet for, e.g. discharge or recycle. In one practice, the inlet is placed at or near the middle of the knock-out pot. The inlet may be perpendicular to the plane of the cylinder or optionally tangential to the plane of the cylinder.

In one practice, the knock-out pot has an outlet located at or near the bottom which acts as an exit for discharge of any liquid de-entrained; in another practice, the knock-out pot has an outlet located at or near the top which acts as an exit to allow vaporized feed, e.g., 1230xa, to go into reactor. Optionally, a section of mesh or, more preferably packing (as known in the art, including without limitation Pall rings and the like and combinations of same) may be installed between the inlet and the top outlet to aid in separation of additional liquid mist or particles. Once the feed, such as 1230xa, enters the knock-out pot, any liquid therein would collect at the bottom of the pot while vapor would go through the top exit to reactor. Since the collected liquid will not contact the catalyst, the catalyst life will be improved.

In another embodiment, the de-entrainer is a tower (which term includes one or more towers which can be the same or different) which may be used alone or in combination with another de-entrainer, e.g. a knock out pot as described above. The tower may be a packed tower, a trayed tower or combinations thereof; in one practice, the tower is a packed tower wherein the packing comprises random packing, structured packing, vane assemblies (e.g. Flexichevron®), demisters, and the like, or a combination thereof.

In another embodiment, the invention relates to a process to prepare 2-chloro-3,3,3,-trifluoropropene (1233xf) comprising Steps (a), (b), and (c). In Step (a), a starting material is provided, preferably selected from one or more chlorinated compounds according to Formulae I, II and/or III:

$$CX_2\!=\!CCl\!-\!CH_2X \quad\quad\quad\quad (\text{Formula I})$$

$$CX_3\!-\!CCl\!=\!CH_2 \quad\quad\quad\quad (\text{Formula II})$$

$$CX_3\!-\!CHCl\!-\!CH_2X \quad\quad\quad\quad (\text{Formula III})$$

wherein X is independently selected from F, Cl, Br, and I, provided that at least one X is not fluorine; Preferably, these compounds contain at least one chlorine, more preferably a majority of X is chlorine, and even more preferably all X is chlorine. Preferably, the method generally comprises at least three reaction steps. In one practice, the starting material is 1,1,2,3-tetrachloropropene (1230xa, also known as TCP). In another practice, the starting material is 1,1,1,2-tetrachloropropene (1230xf); in another it is 1,1,1,2,3-pentachloropropane (240db). Other starting materials as known in the art and combinations of same are contemplated. The starting material, e.g. 1230xa, is in the vapor and liquid (unvaporized) state. As appreciated by the artisan, 1230xa has high boiling point (162° C. @ 743 torr) and therefore has to be vaporized, typically in a vaporizer before it enters the vapor phase fluorination reactor. It has now been found that unvaporized liquid 1230xa that is leftover in the vaporizer can entrain and cause the deactivation of the catalyst; moreover, it has now been found that during the vaporization of 1230xa some oligomers can also form, which can also deactivate the catalyst. Among other things, the practice of the invention removes (in the separating step of the invention) this entrained liquid and/or oligomers and/or any compounds that have boiling point higher than the temperature of vaporizer.

Step (b) of the inventive process comprises separating the vaporous starting material (e.g. 1230xa) from the liquid starting material (e.g. 1230xa); and Step (c) is contacting the vaporous starting material (e.g. 1230xa) with hydrogen fluoride HF under conditions effective to form 1233xf. Preferably, the conditions effective include the presence of a fluorination catalyst selected, without limitation, from the group consisting of $Cr_2O_3$, $FeCl_3/C$, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$, $NiCl_2/AlF_3$, fluorinated species of $Cr_2O_3$, and mixtures thereof. Fluorinated species of $Cr_2O_3$ are preferred.

In a preferred practice, separating step (b) occurs in a de-entrainer (which term includes one or more de-entrainers) as herein described.

The invention may be employed, for example, as part of a larger process to make compounds such as 2-chloro-1,1,1,2-tetrafluoropropane (HCFC-244bb), and 2,3,3,3-tetrafluoropropene (1234yf). For example, the process of the invention can be the first of the three-step process to make 1234yf as described above.

In a preferred embodiment, the process of the invention includes, without limitation, the following steps: (a) flowing HF and 1230xa through a vaporizer and periodically opening the knock out pot to drain any liquid that has pooled in the pot; (b) subjecting the substantially vaporous (pure) 1230xa feed to conditions effective that fluorinate at least a portion of the 1230xa feed to produce a reaction product comprised HFO-1233xf; in one practice this reaction product comprises more HFO-1233xf as compared to a reaction product produced using a 1230xa feed that contains some 1230xa in the liquid form, i.e. using a feed not subject to de-entrainment as described herein. The practice of the invention whereby a substantially liquid free feed of 1230xa is effective to prolong catalyst life. Methods to make 1230xa are disclosed, e.g., in U.S. Pat. No. 3,823,195; and the invention can apply to methods of making 1233xf as disclosed, e.g., in U.S. application Ser. No. 12/338,466, the contents of both of which are incorporated herein by reference.

In one embodiment of the invention, for vapor-phase hydrofluorination to produce 1233xf, after de-entrainment as per the invention, hydrogen fluoride gas (HF) and 1230xa are fed continuously through the catalyst bed in a vapor phase fluorination reactor. The mol ratio of HF to 1230xa is about 1:1 to about 50:1 and preferably from about 10:1 to about 20:1. The reaction between HF and 1230xa is preferably carried out at a temperature from about 150° C. to about 400° C. (preferably from about 150° C. to about 350° C.) and at a pressure of about 0 psig to about 500 psig (preferably from about 20 psig to about 200 psig). The catalyst may be unfluorinated or preferably a fluorinated chromium oxide. The catalyst may (or may not) be activated with anhydrous hydrogen fluoride (hydrogen fluoride gas) before use depending on the state of the catalyst.

The hydrofluorination reaction is preferably carried out to attain a conversion of about 50% or higher, preferably, about 90% or higher. Conversion is calculated by the number of moles of reactant (1230xa) consumed divided by number of moles of reactant (1230xa) fed to the reactor multiplied by 100%. The selectivity for 1233xf attained is preferably about 60% or higher, and more preferably about 80% or higher. Selectivity is calculated by number of moles of product (1233xf) formed divided by number of moles of reactant consumed multiplied by 100%.

Hydrofluorination may be carried out in a corrosion-resistant reaction vessel. Examples of corrosion-resistant materials are Hastelloy, Nickel, Incoloy, Inconel, Monel and fluoropolymer linings. The vessel is a fixed catalyst bed or fluidized bed. If desired, inert gases such as nitrogen or argon may be employed in the reactor during operation.

The foregoing hydrofluorination steps are not necessarily limiting to the instant invention, however, and may also include derivative or alternative methodologies that are otherwise known in the art.

Preferably, before 1230xa is fed into the fluorination reactor, it is dried. The non-limiting examples of the drying media are 3A Mol Sieve and Drierite®.

Preferably, the contact time of the 1230xa with the catalyst may range from about seconds 15 to about 60 seconds, however, longer or shorter times can be used.

In general, the effluent from the fluorination reaction step, including any intermediate effluents that may be present in multi-stage reactor arrangements, may be processed to achieve desired degrees of separation and/or other processing. For example, in embodiments in which the reactor effluent comprises 1233xf, the effluent will generally also include HCl, HF, 1232xf, 244bb, and unreacted 1230xa. Some portion or substantially all of these components of the reaction product may be recovered from the reaction mixture via any separation or purification method known in the art such as neutralization and distillation. It is expected that unreacted 1230xa and HF could be recycled, completely or partially, to improve the overall yield of the desired 1233xf. 1232xf and any 1231 isomers formed can also be recycled. Optionally but preferably, hydrogen chloride is then recovered as the result of the fluorination reaction. Recovery of hydrogen chloride is conducted by conventional distillation where it is removed as the distillate.

Alternatively, HCl can be recovered or removed by using water or caustic scrubbers. When a water extractor is used HCl is removed as an aqueous solution. When caustic is used, HCl is just removed from system as a chloride salt in aqueous solution.

HCl may also be fed to the next reaction step along with 1233xf as disclosed in pending application Ser. Nos. 12/512,955 and 12/611,288.

The following are examples of the invention and are not to be construed as limiting.

Example 1

This example illustrates a practice of the invention directed to the continuous operation of 1230xa fluorination to make 1233xf in the presence of a knock-out pot located between vaporizer and reactor. The catalyst used in experiment was fluorinated chromium oxide.

About 6.5 L of fluorinated chromium oxide was loaded in 4" tube reactor. The reaction was carried out at initial 200° C. and up to 260° C. The reaction pressure was 70 psig. HF and 1230xa/1233xf (90:10 weight ratio) flowrates were 3.3 and 1.6 lb/hr, respectively. The conversion of 1230xa was 100%. The average selectivity to 1233xf was ~90%. The experiment ran continuously for about 6000 hours. The knock-out pot was emptied after the experiment. About 5.8 g of dark brown solution was collected. The GC analysis of the dark brown solution indicated 82.3% 1230xa and 17.7% of unknowns. GC-MS analysis identified several components including 1233xf, 1232xf, 242 isomer, 1231xd, 1230xa, $C_6HF_4Cl_3$, $C_6H_3F_6Cl_3$, etc.

Comparative Example 1

No knock-out pot is used in this example. About 6.5 L of fluorinated chromium oxide is loaded in 4" tube reactor. The reaction is carried out at initial 200° C. and up to 325° C. The reaction pressure is 70 psig. HF and 1230xa/1233xf (90/10 weight ratio) flowrates are set at 3.3 and 1.67 lb/hr, respectively. The conversion of 1230xa is initially 100%. The catalyst shows signs of deactivation at about 100 hours, evidenced by a drop in conversion of 1230xa. Temperature is increased in 5° C. increments to maintain a conversion of about 70% while maintaining an average selectivity to 1233xf at ~90%. After about 350 hours and a temperature of 300° C. is reached, the selectivity to undesired components increases. Experiment is discontinued after about 400 hours. It is concluded that, among other causes, liquid entrainment contributes to the rapid deactivation of the catalyst.

What is claimed is:

1. A process to prepare 2-chloro-3,3,3,-trifluoropropene (1233xf) comprising:
   (a) providing a starting material comprising liquid 1,1,2,3-tetrachloropropene (1230xa) and vaporous 1230xa;
   (b) separating the vaporous 1230xa from the liquid 1230xa; and
   (c) contacting the vaporous 1230xa with hydrogen fluoride HF under conditions effective to form 1233xf.

2. The process of claim 1 wherein the conditions effective include the presence of a fluorination catalyst.

3. The process of claim 2 wherein the fluorination catalyst is selected from the group consisting of $Cr_2O_3$, $FeCl_3/C$, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$, $NiCl_2/AlF_3$, fluorinated species of $Cr_2O_3$, and mixtures thereof.

4. The process of claim 1 wherein the separating step (b) occurs in a de-entrainer.

5. The process of claim 4 wherein the de-entrainer is a tower, a knock out pot, a filter, or combinations thereof.

6. The process of claim 5 wherein the de-entrainer is a knock-out pot, the knock out pot optionally comprising an internal coalescer.

7. The process of claim 6 wherein the internal coalescer comprises packing, mesh, or combinations thereof.

8. The process of claim 7 wherein the packing comprises Pall rings.

9. The process of claim 5 wherein the tower is a packed tower, a trayed tower, or combinations thereof.

10. The process of claim 9 wherein the tower comprises a packed tower.

11. The process of claim 10 wherein the packed tower comprises random packing, structured packing, vane assemblies, demisters, or combinations thereof.

12. A process to produce 2-chloro-1,1,1,2-tetrafluoropropane (HCFC-244bb) comprising contacting 2-chloro-3,3,3,-trifluoropropene (1233xf) as produced according to claim 1 with hydrogen fluoride (HF) under conditions effective to form 244bb.

13. A process to produce 2,3,3,3-tetrafluoropropene (HFO-1234yf) comprising contacting 2-chloro-1,1,1,2-tetrafluoropropane (HCFC-244bb) as produced according to claim 12 with a dehydrochlorination catalyst under conditions effective to form 1234yf.

14. A method to extend catalyst life for a vapor phase fluorination catalyst used in producing 1233xf comprising:
   (a) vaporizing 1230xa wherein a portion of the 1230xa remains unvaporized;
   (b) separating the unvaporized portion of the 1230xa from the vaporized portion of the 1230xa; and
   (c) feeding the vaporized portion of the 1230xa to a reactor comprising a vapor phase fluorination catalyst in the presence of HF under conditions effective to form 1233xf,
   wherein the life of the vapor phase fluorination catalyst is extended as compared to the life of the catalyst when there is no separation step (b) and vaporized and unvaporized 1230xa is fed to the reactor.

15. A process to prepare 2-chloro-3,3,3,-trifluoropropene (1233xf) comprising:
   (a) providing a starting material comprising liquid 1,1,1,2-tetrachloropropene (1230xf) and vaporous 1230xf;
   (b) separating the vaporous 1230xf from the liquid 1230xf; and (c) contacting the vaporous 1230xf with hydrogen fluoride HF under conditions effective to form 1233xf.

16. A process to prepare 2-chloro-3,3,3,-trifluoropropene (1233xf) comprising:
- (a) providing a starting material comprising liquid 1,1,1,2,3-pentachloropropane (240 db) and vaporous 240db;
- (b) separating the vaporous 240db from the liquid 240db; and
- (c) contacting the vaporous 240db with hydrogen fluoride HF under conditions effective to form 1233xf.

* * * * *